United States Patent [19]

DuFault

[11] Patent Number: 4,799,493
[45] Date of Patent: Jan. 24, 1989

[54] DUAL CHANNEL COHERENT FIBRILLATION DETECTION SYSTEM

[75] Inventor: Robert A. DuFault, Roseville, Minn.

[73] Assignee: Cardiac Pacemakers, Inc., St. Paul, Minn.

[21] Appl. No.: 25,811

[22] Filed: Mar. 13, 1987

[51] Int. Cl.$^4$ .............................................. A61B 5/04
[52] U.S. Cl. ............................... 128/705; 128/419 D; 128/419 PG
[58] Field of Search ........ 128/696, 704, 705, 419 PG, 128/419 D

[56] References Cited

U.S. PATENT DOCUMENTS

| | | | |
|---|---|---|---|
| 4,537,200 | 8/1985 | Widrow | 128/696 |
| 4,543,963 | 10/1985 | Gessman | 128/419 PG |
| 4,557,266 | 12/1985 | Schober | 128/419 PG |

Primary Examiner—Francis J. Jaworski
Assistant Examiner—George Manuel
Attorney, Agent, or Firm—Orrin M. Haugen; Thomas J. Nikolai; Frederick W. Niebuhr

[57] ABSTRACT

A tachyarrhythmia/fibrillation detector in which the Widrow-Hoff LMS algorithm is utilized for estimation of a transfer function. One or more LMS cancellers are placed between two separate sensing electrode pairs placed in or on the heart and by noting the convergence of the error signal or the lack thereof the type of tachyarrhythmia or a ventricular fibrillation condition can be discerned. With sinus rhythm, the error signal is small in power compared to the power of the desired response. With ventricular fibrillation, however the filter weights are unable to converge to cause the filter output signal to track desired signal and the filter output waveform becomes asynchronous with the desired response, yielding a detectably high error power.

4 Claims, 6 Drawing Sheets

```
       SINUS RHYTHM
         | VENT. TACHY.
         |   | ADAPTIVE
         |   |   | RATE
         ↓   ↓   ↓   ↓

0   0   0   0    OFF, INITIALIZING
         0   0   0   1    WPW, CONCEALED RETROGRADE PATH
         0   0   1   0    PROBABLE MALFUNCTION
         0   0   1   1    PROBABLE MALFUNCTION
         0   1   0   0    SINUS RHYTHM (SR)
         0   1   0   1    SUPRA-VENTRICULAR TACHY. (SVT)
         0   1   1   0    TRANSITION, VT TO SR
         0   1   1   1    TRANSITION, VT TO SVT
         1   0   0   0    SLOW VT OR STABLE ABERRANT CONDUCTION (BBB)
         1   0   0   1    DOMINANT MONOMORPHIC VT
         1   0   1   0    PROBABLE MALFUNCTION
         1   0   1   1    DOMINANT VT, TRANSITION FROM SR
         1   1   0   0    SLOW SECONDARY VT, OR BBB
         1   1   0   1    STABLE VT, SECONDARY PATTERN
         1   1   1   0    SLOW VF, OR TRANSITION TO SLOW SECONDARY VT
         1   1   1   1    VF, OR TRANSITION TO SECONDARY VT
```

ASSUMES TWO FIXED FILTERS WHICH REMEMBER PRIMARY VT AND SR PATTERNS, A THIRD FILTER CONTINUOUSLY ADAPTIVE, AND A RATE COUNTER DICHOTOMIZED TO "FAST" AND "SLOW".

DUAL CHANNEL COHERENT FIBRILLATION DETECTION SYSTEM

BACKGROUND OF THE INVENTION

I. Field of the Invention:

This invention relates generally to biomedical apparatus; and more particularly to a system for detecting the onset of tachyarrhythmias, such as ventricular fibrillation whereby effective intervention can be initiated to restore the patient to normal sinus rhythm.

II. Discussion of the Prior Art:

To better comprehend the prior art, it is deemed necessary to explain the physiologic characteristics of the heart which might be used for distinguishing between normal sinus rhythm (SR), ventricular tachycardia (VT), supra-ventricular tachycardia (SVT) and ventricular fibrillation (VF). In SR, there is a synchronized depolarization of the cardiac cells resulting in the conventional QRS electrogram waveform. In VF, however, the cardiac cells generally lose their synchrony and the depolarization of one cell or group of cells no longer bears any particular relationship to the depolarization of other cell groupings resulting in a loss of distinct rhythm. Not only does the rhythm become indistinct but morphological changes also occur such that the beats are no longer of uniform shape due to the fact that the number of cells participating in each independent and nonsynchronized depolarization also changes.

Known VT and VF sensing techniques have involved the use of a bipolar or unipolar catheter disposed proximate the right ventricular apex for detecting signals occasioned by the cell depolarization and the use of a counting algorithm in an attempt to distinguish between SR, VT and VF on the basis of pulse rate. In connection with that algorithm, VF is considered to be a heart rate that is greater than some certain value typically exceeding rates associated with VT.

It is also found that the transition from SR to either VT or VF is generally accompanied by a fairly severe change in morphology or pulse shape because the overall pattern of depolarization and timing between cell changes when passing from SR through the onset of VT. A number of pulse counting techniques described in the literature depend not only upon determining the rate of the tachycardia, but also on the so-called "rate of onset". That is to say, they not only assess the absolute pulse rate but how rapidly the tachycardia begins relative to sinus rhythm. Investigators have determined that absolute rate alone is not a reliable indicator of VT or SVT in that high SR may be physiologically appropriate due to physical activity or even sudden fright resulting in autonomic stimulus to the heart. The "rate-of-onset measure" is generally based upon a threshold criteria determined by how rapidly the interval between successful QRS complexes is changing. Even when rate-of-onset considerations are relied upon in conjunction with absolute rate, known prior art detection apparatus still may mistake physiologically appropriate tachycardias from the non-appropriate tachycardias, i.e., there is an overlap in the domain which could contribute to inappropriate intervention. Moreover, pulse morphology changes have frequency extensions, as well, which may affect detection circuit performance. This may occur precisely at the critical point where rate-of-change information is needed for rate determination. Thus rhythm discrimination techniques which depend on rate and rate-of-change measurements may fail on two counts: rate overlap and misidentified rate changes.

Another known approach for identifying and discriminating the states and transitions between SR, SVT, VT and VF is based upon measurements on the cardiac electrogram and utilizes a frequency analysis technique which is used in determining the rhythm from the power spectrum. This technique is limited to the surface ECG by computational requirements. Still other techniques attempted for identifying and discriminating between normal SR and various tachycardias and fibrillation involve morphologic measures, such as rise time or polarity of the ECG waveform and the so-called "probability density function (PDF)" measurements in which the cardiac waveform is characterized by the relative percentage of time that it spends at various amplitude levels.

Each of these techniques has significant shortcomings. The outcome of the evaluation involving the PDF, for example, is found to be quite dependent upon electrode placement and the evaluation function requires an inordinate amount of time. Implantable tachyarrhythmia control devices have a variety of responses keyed to specific arrhythmias. The appropriate response is selected and triggered by the arrhythmia detection circuit. Inappropriate or missed detections carry significant penalties.

While maintaining accuracy, arrhythmia recognition, especially for VF, must be prompt. Shortening the interval from VF onset to intervention results generally in a higher proportion of successes due to halting the decay of the cardiac substrate before that process becomes irreversible. While it is not yet clear that this benefit extends to the first 30 seconds following onset, it is still vital that recognition, which controls the entire process leading to intervention, be as accurate and timely as possible. In the presence of SR and SVT, however, intervention is inappropriate. False identification of SR or SVT as VT or VF can lead to potentially dangerous intervention, again confirming the need for accuracy.

In contrast to the prior art, the present invention relies upon a spacial coherence detection approach to tachyarrhythmia discrimination. It was observed that the morphologic and probability density function techniques referred to above depended on a determination of the temporal departure from synchronization on a beat-to-beat basis. This, however, results from and is secondary to spacial decorrelation over the entire cardiac domain. It was felt that the temporal detector, based upon signals picked up by a single lead, would take an inordinate amount of time from the onset of VF or VT due to the degree of spacial desynchronization that must occur in order to appear locally on such a single lead. In the case of the present invention, a measurement is taken of the spacial decorrelation directly. Instead of using a single sensing electrode, one or more leads having plural electrodes are implanted within the heart but at somewhat remote locations with respect to one another, assuring that substantially distinct segments of cardiac tissue dominate the electrical field surrounding each electrode. As a result, the dominant electrical activity influencing one lead tends to be somewhat independent from the electrical activity influencing the other lead. During SR, each electrode receives some contribution from every electrically active cardiac cell. While the resulting QRS complex may appear quite different on the two leads, these signals are substantially coherent in the sense that there is a linear relationship between them. That is, QRS wave on one lead may be derived from that on the other via a linear transfer function. Assuming that the leads are mature and stable in the sense that they do not move, the transfer function also will be stable and will consistently reproduce the signal on one lead from that on the other.

During VT, the QRS morphology on both leads will, in general, appear different than during SR or SVT. This difference reflects the change in the depolarization sequence, as the depolarization wave travels through the muscle tissue, rather than the Purkinje fibers. In stable, monomorphic VT, the signals on the two leads will again be substantially coherent, but with different linear relationship than that which describes SR. Stated otherwise, a different transfer function is required to convert the signal on one lead to that of the other.

During VF, the depolarization sequence is constantly modifying from beat-to-beat, with dispersal of the depolarization sequence occurring to the point where cardiac activity can no longer be characterized as a sequence of beats, but rather as continuous, fragmented electrical activity.

The concept of coherence and the implied existence of linear transfer function depend on the existence of a persistent linear relationship. Taking the ratio of the complex spectra of the electrode signals over a specific time interval produces a result which resembles a transfer function, but does not carry with it the weight of persistence. Thus, such a function could be derived for every interval during the course of fibrillation, but the result would be inconsistent and incoherent. A stable transfer function cannot be said to exist under these circumstances. Thus, during VF, not only the signal morphology is changing, but the channel characteristics between leads, as reflected in the transfer function, is likewise changing.

SUMMARY OF THE INVENTION

In accordance with the present invention, a method and apparatus is provided for detecting and discriminating between sinus rhythm, ventricular tachycardia, supra-ventricular tachycardia and ventricular fibrillation. The technique involves applying the least-mean-squares (LMS) algorithm first described by B. Widrow and M.E. Hoff in "Adaptive Switching Circuits", IRE WESCON Convention Record, Part 4, pp. 96–104, Sept. 1960, and elaborated subsequently by Professor Bernard Widrow in a book captioned "Adaptive Signal Processing", Prentice-Hall Publishing Company, 1985, which estimates the transfer function or channel characteristics between a signal (or noise) source and the perceived signal plus noise. This signal processing technique is used to implement coherence analysis between two sources of cardiac electrical activity, one of which is sensed on a local basis using an endocardial bi-polar lead and one sensing more global activity such as may be obtained between two spaced surface ring electrodes on an endocardial lead. During sinus rhythm, the vector difference is essentially constant and is estimated as a transfer function by the LMS algorithm. This transfer function is then used to estimate the global electrogram from the local. The estimate is then substracted from the actual, leaving a null output. In the presence of VT, the vector difference changes and results in non-zero output from the null, until the channel characteristics are re-estimated. In VF, the vector difference is constantly changing and the channel characteristics can no longer be estimated. Therefore, during VF, the "null" output is constantly changing and does not fall to zero. Thus, by monitoring the "error" signal emanating from the LMS adaptive filter, one can readily detect a shift from SR to VF. Similarly, in tachyarrhythmia discrimination, several LMS adaptive filters may be coupled to the dual leads and by appropriately causing each to adapt and, therefore, null a different rhythm and by noting the rate range, VT can be distinguished from SR and VF.

OBJECTS

It is accordingly a principal object of the present invention to provide an improved system and method for detecting and identifying diverse cardiac rhythms.

Another object of the invention is to provide a system and apparatus for sensing ventricular fibrillation and for automatically activating appropriate intervention.

Yet another object of the invention is to provide an apparatus and method for distinguishing between sinus rhythm, ventricular tachycardia and ventricular fibrillation in a more reliable fashion than has been possible using prior art techniques.

A yet further object of the invention is to provide a system in which dual leads or plural electrodes on a single lead are appropriately located within a ventricular chamber of the heart and coupled to an LMS adaptive filter for detecting a particular cardiac rhythm by noting the magnitude of the error output of that filter.

DESCRIPTION OF THE DRAWINGS

These and other objects and advantages of the invention will become apparent from the following detailed description of the preferred embodiment, especially when considered in conjunction with the accompanying drawings in which.

DESCRIPTION OF THE PREFERRED EMBODIMENT

Figure 1:
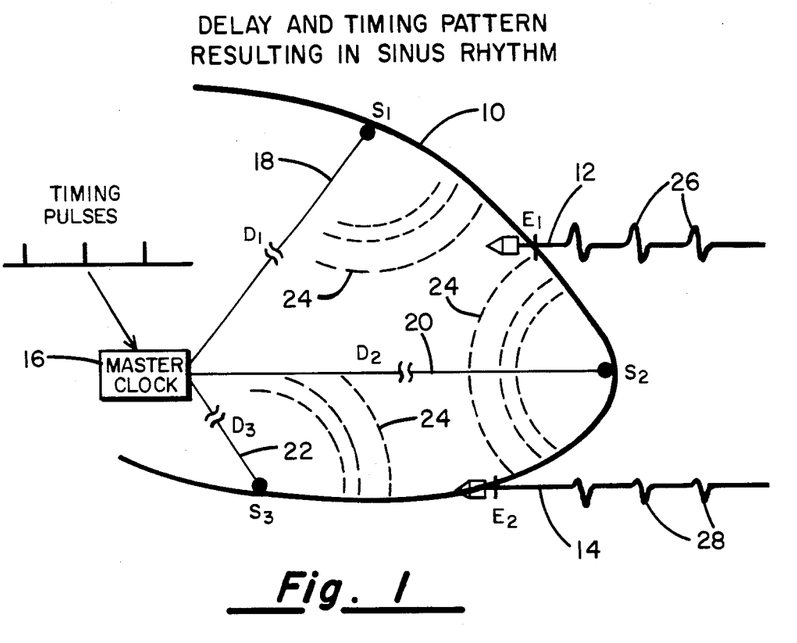
FIG. 1 is a schematic of electrical activity of a heart in sinus rhythm.
Figure 2:
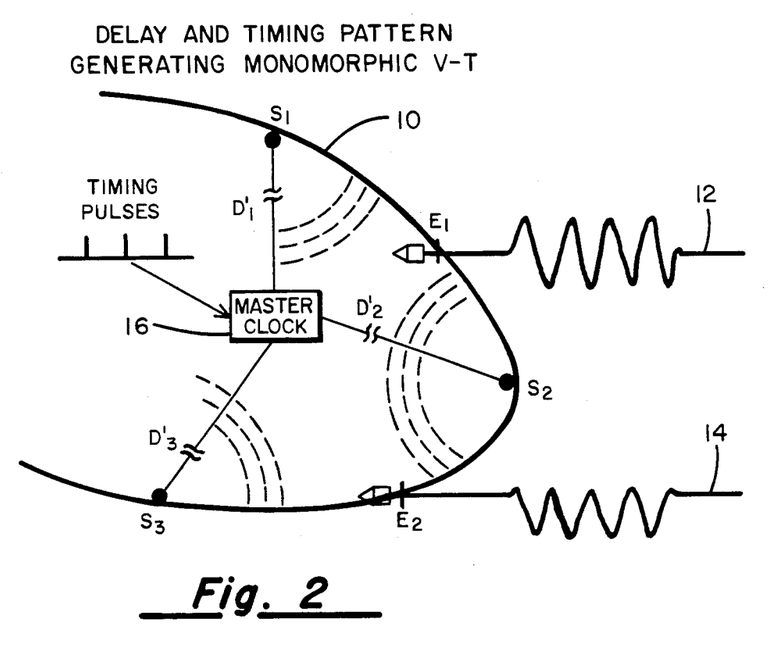
FIG. 2 is a schematic illustration of a heart in ventricular tachycardia.
Figure 3:
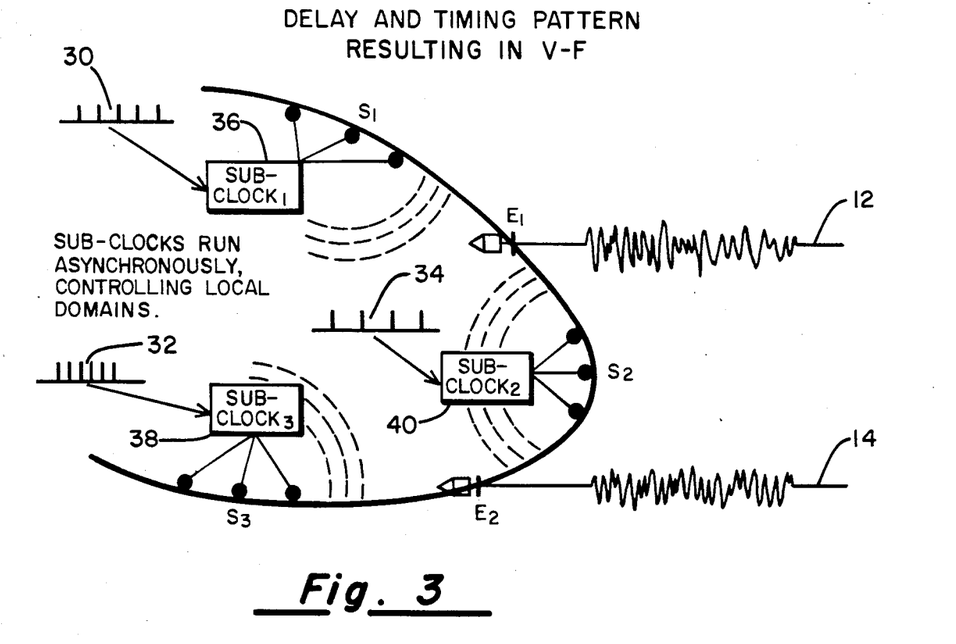
FIG. 3 is a schematic illustration of a heart in a state of ventricular fibrillation.

Referring to FIGS. 1 through 3, there is shown in schematic form a model of how the heart behaves during sinus rhythm, tachycardias and during ventricular fibrillation, respectively.

In FIG. 1, a ventricular section of the heart is identified by the numeral 10 in which or on which two distinct catheters 12 and 14 have been implanted. Catheter 12 has an electrode $E_1$ in contact with the heart tissue while catheter 14 has a corresponding electrode $E_2$. Schematically representing the sinus node or the supraventricular source is a master clock 16 which provides regularly occurring timing pulses which are distributed to various points in the heart, via the cardiac conduction system, represented by the delay paths 18, 20 and 22. The dotted line arcs as at 24 represent the propagation of the cardiac cell depolarization fields, finally impinging on the sensing electrodes. Each of the electrodes $E_1$ and $E_2$ senses the composite depolarization activity from all over the heart, but the effect of each specific cellular depolarization field depends on the distance to each electrode and its relative timing.

Because the position of the two electrodes is different and because the orientation of the electrode relative to its indifferent electrode may also be different, the resulting signal waveforms 26 and 28 picked up by the electrodes generally will have differing morphologies during sinus rhythm. The QRS signals picked up by the electrodes in FIG. 1 are a composite projection of a consistent pattern of cellular electrical activity, schematically represented as being triggered through a system of fixed delays by each pulse of a common clock. While these signals may appear quite different on the two leads, they are substantially coherent in the sense that there is a persistent linear relationship between them. The QRS on the lead 12 may, therefore, be deduced from that on the lead 14, and vice-versa, by a linear process or transfer function. Convolving one signal with a filter derived from the transfer function will reproduce the other signal.

With respect to FIG. 2, there is a similar depiction of the heart 10 during an episode of ventricular tachycardia. In comparing FIGS. 1 and 2, the chief distinction is that a different pattern of delays times the cellular depolarizations, depicted by a shift in the master clock 16 position. (The positions shown have no specific significance other than to indicate a change in timing.) Thus, in stable monomorphic VT, all cells are driven by a master clock through a different pattern of delays than those which persist in SR. The QRS morphology on each of the leads 12 and 14, in general, appears different from their observed counterparts during sinus rhythm, which is a result of the change in the depolarization sequence. However, the two signals are, again, substantially coherent, but with a different linear relationship reflecting the altered cellular depolarization order, or delay pattern. Therefore, a different transfer function is required to convert the signal on one lead to that on the other. The similarity between sinus rhythm and ventricular tachycardia is that each cardiac cell depolarizes once, and only once, during a cardiac cycle. However, the timing is no longer controlled by the Purkinje system, but by the relative distance from the ectopic focus that is stimulating the ventricular tachycardia. As with sinus rhythm, in ventricular tachycardia, a consistent pattern of delays and attenuations prevail, but a different timing pulse period go into the master clock 16 and a different system of delays and attenuation exit the master clock. The important thing to note is that with ventricular tachycardia a consistent linear process exists between the two electrodes and a transfer function relating the two signals to one another can be estimated.

FIG. 3 is intended to depict the gradual breakdown which occurs when progressing into a ventricular fibrillation. The schematic illustration depicts the heart as being controlled by a number of subclocks, each controlling a small domain within the heart and these domains may, in effect, run at different rates as illustrated by the different timing pulse patterns 30, 32, 34 shown as entering the subclocks 36, 38 and 40. It is found that these rates may also change in an inconsistent and continuous fashion. Because of relative tissue proximity, each lead is dominated by electrical activity under control of a different clock. As such, the net result of electrodes $E_1$ and $E_2$ in FIG. 3 is that they sense cardiac activity over the entire heart, but the spacial decorrelation manifests itself as a temporal decorrelation on leads 12 and 14. A consistent transfer function no longer exists between the leads due to the face that the system of subclocks are clocking rates as well as attenuations and delays is changing in a continuous and inconsistent fashion.

Thus it can be seen that estimating the transfer function offers a means for discriminating between tachyarrhythmias. The transfer function, once determined, generates an accurate replica (estimate) of the signal on one lead from that on the other, which can be subtracted from the reference to form a null for stable rhythm. A filter tuned to produce a null to sinus rhythm will also null SVT, since the depolarization sequence has little dependence on rate in a healthy heart. Monomorphic VT is also sufficiently stable to produce a null by this means. However, a filter tuned to null sinus rhythm or SVT will not, in general, null VT. The converse of the latter statement is also true. Since the relationship is constantly changing, it is not possible to null VF consistently. Failure to produce a stable transfer function is a hallmark of VF. Moreover, filters tuned to null SR or VT will both produce an error output in the presence of VF.

It has been stated that the complex ratio of Fourier transforms of the signals on the two leads produces a result which resembles a transfer function, but does not carry with it the idea of persistence. There are, however, techniques for estimating a transfer function in which such a ratio is calculated for each of many adjacent intervals. The separate coefficients are then allowed to average, or adapt, to their final result by averaging over all the intervals. While implementable on a general purpose computer, this is a formidable task for an implantable device. The LMS estimation technique was chosen because it is simple computationally and, therefore, more suited to an implantable device. While it has shortcomings relative to the more general technique, these shortcomings do not prevail in this application.

Figure 4:
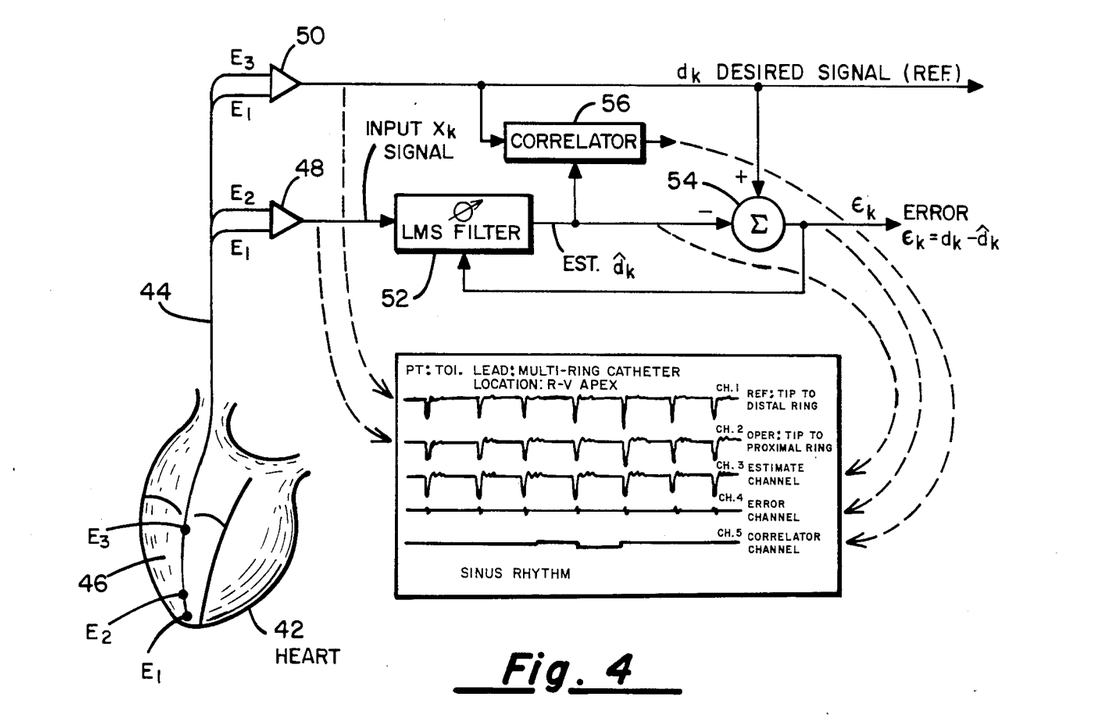
FIG. 4 depicts the manner in which signals derived from a multi-electrode lead located near the right ventricular apex in the right ventricle are applied to a LMS filter along with waveforms showing the input and output relationship.

In accordance with the present invention, ventricular activity is sensed on two separate endocardial leads, e.g., a right ventricular apex bipolar lead and a right ventricular multi-ring catheter. The signals are applied to a variable transfer function, LMS filter of the type described by Bernard Widrow et al in a paper entitled "Adaptive Noise Cancelling: Principles and Applications", Proc. IEEE, Vol. 63, Vec. 1975. More particularly, and with reference to FIG. 4, numeral 42 again refers to a schematic representation of the heart with a multi-electrode lead 44 positioned in the right ventricle chamber and having a tip electrode $E_1$ at the right ventricular apex and ring electrodes $E_2$ and $E_3$ positioned proximally to effect primarily local near field activity between $E_1$ and $E_2$ and primarily global far field activity between $E_1$ and $E_3$ spaced-apart locations. Conductive wires running through the body of the lead 44 connect electrodes $E_1$ and $E_2$ to a first differential amplifier 48 while conductors couple electrodes $E_1$ and $E_3$ to a differential amplifier 50. Adopting the designations utilized by Professor Widrow in the above-cited references, the output from the differential amplifier 48 comprises the input signal vector $= [x_{0k}, x_{1k} ... x_{(n-1)k}]$, to the LMS adaptive filter 52, wherein k is the time index. The signal emanating from differential amplifier 50 is defined as the desired signal $d_k$ and is applied to a summing node 54 along with the output from the LMS adaptive filter 52. The output from the adaptive filter 52 is the "estimate" signal $Y_k$. The output from the summation node 54 then comprises the error signal $E_k$ that is the difference between the desired or reference signal $d_k$ and the estimated siganl $Y_k$. Also depicted in the block diagram of FIG. 4 is a correlator 56 which receives as its inputs the desired signal $d_k$ and the estimate signal $Y_k$ and yields the output (1-R), where R is the correlation coefficient. When the leads are detecting sinus rhythm and the filter has locked onto that, the correlation coefficient R is high, and the output from the correlation channel, (1-R), is low (zero). During VF, however, the estimate $Y_k$ poorly approximates $d_k$. Therefore, R is low and the (1-R) output will go high.

To better understand the fibrillation detection system of FIG. 4, that figure also includes signal traces corresponding to data taken from a human patient undergoing cardiac electrophysiology laboratory procedures. Because of the particular lead arrangement, the two channels have substantially parallel electrical vectors with common local components from electrode $E_1$ and with the desired channel incorporating differential amplifier 50 receiving a stronger global contribution. An examination of the waveforms of the outputs from the differential amplifiers 48 and 50 reveal that the two channels exhibit substantial morphologic similarity particularly during sinus rhythm. The low residual error signal $E_k$ is indicative of sinus rhythm and indicates a stable transfer function.

The LMS adaptive filter algorithm can be implemented using analog to digital converters and a programmed microprocessor for computing the various parameters. Using state-of-the-art technology, it is thought that the technique can be adapted to implantable devices.

Figure 5:
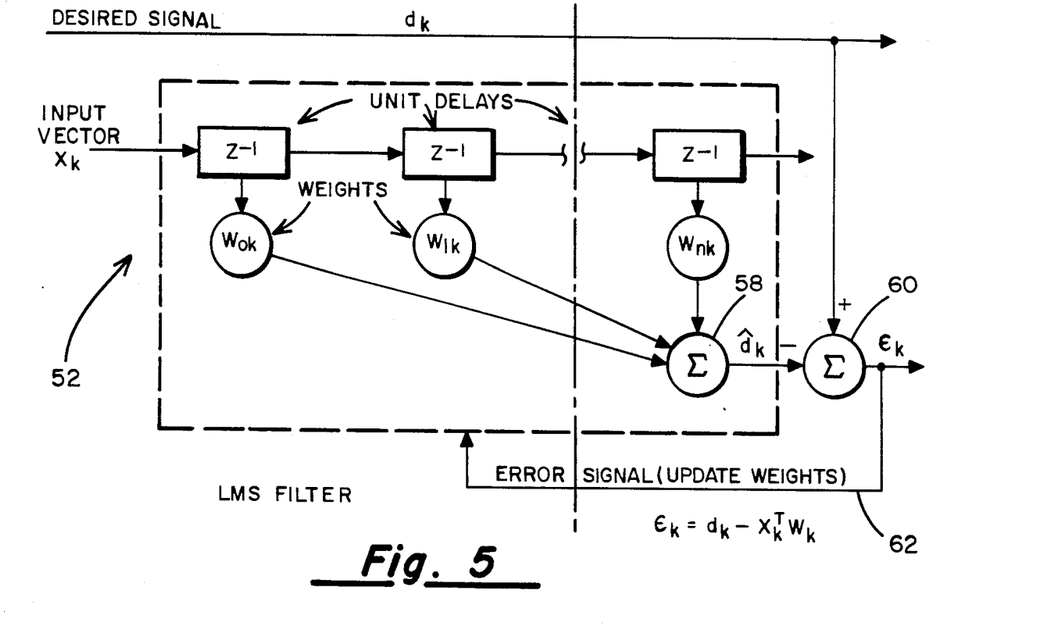
FIG. 5 is a block diagram representation of the LMS adaptive filter.

Having described in general terms with the aid of FIG. 4 the adaptation of the LMS adaptive filter to the discrimination between SR, VT and VF, it is believed helpful to a complete understanding of the present invention to set out in greater detail the implementation of the LMS adaptive filter. In this regard, reference will be made to the block diagrams of FIGS. 5 and 6. FIG. 5 is an aid to understanding the LMS algorithm when functioning in its filtering mode while FIG. 6 pertains to operation in the up-date mode.

When functioning in the filtering mode (FIG. 5) it behaves as a regular finite impulse response (FIR) linear filter and the vector equation for that can be represented as:

$$E_k = d_k - x_k^T W_k$$

Figure 6:
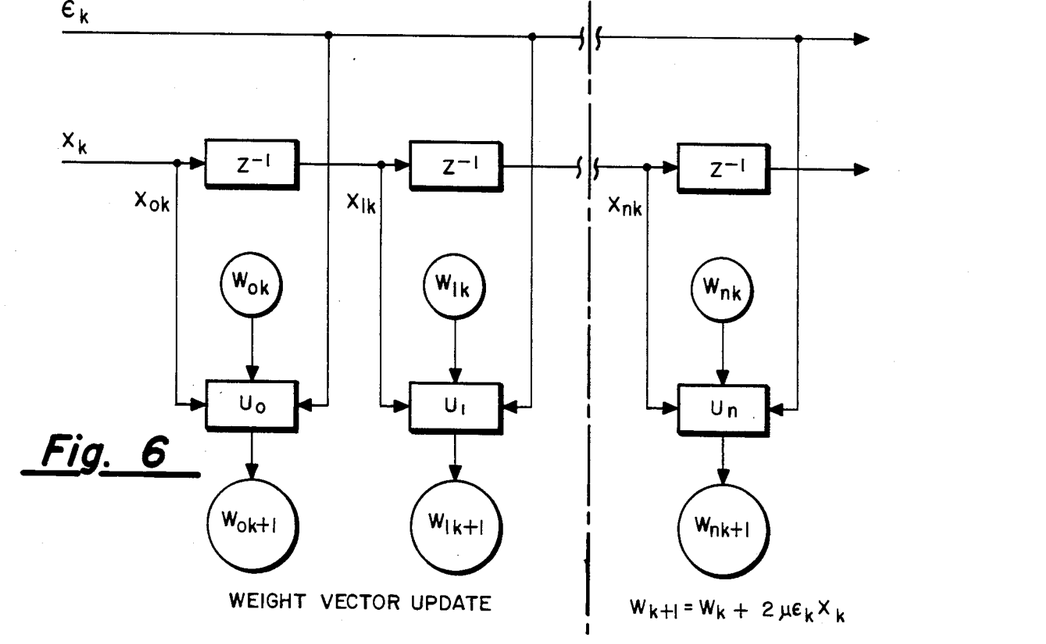
FIG.6 is a block diagram of the update algorithm of the LMS adaptive filter of FIG. 5.

In the above expression, k is a time index, $E_k$ is the error signal at time k, $d_k$ is the instantaneous value of the desired signal at time k, $X_k$ is the input signal vector which is convolved with a weight vector $W_k$ and which indicates that the weights adapt over time to form an output signal $Y_k$ which is an estimate of the value of $d_k$ at the time k. Following the calculation of the vector quantity $d_k$ and $W_k$, the weight vector is updated from $W_k$ to $W_{k+1}$ by the up-date algorithm represented as "U" in FIG. 6. The up-date algorithm can be represented by the eqution:

$$W_{k+1} W_k + 2\mu E_k X_k$$

where $\mu$ is the adaptation time constant. By way of further explanation, if there are, for example, 32 weights which comprise $W_k$, they may be identified as $W_{1k}, W_{2k} ... W_{nk}$ on out to 32, implying that these are the values of the 32 weights at time k. Similarly, the input vector signal $X_k$, which is the input signal at time k, will also have 32 values, i.e., the values at time k, the immediate moment, plus the value at time k−1, k−2, etc., going back 32 sample spaces. The summation of those products is the filter output, $Y_k$, which is subtracted from the immediate signal value $d_k$ to form the immediate error response $E_k$. This error response is both the signal output from the adaptive filter system and the feedback to the updating equation for the weight vector (FIG. 6).

With reference to FIG. 5, the boxes labeled $z^{-1}$ represent unit delays between the elements of the input signal while the weights $w_{0k}$, $w_{1k}$ are represented by the circles immediately below the unit delays. The individual products are summed at 58 to form the output signal $Y_k$. This signal is, in turn, summed with the desired signal $d_k$ at 60 to form the error signal $E_k$ at its output. The error signal is fed back via path 62 for updating the weight vector.

Referring now to FIG. 6, there is shown the means by which the weight elements of the filter of FIG. 5 are updated in response to the value of the error signal. Understanding that a new error output occurs each time a new element of the input signal vector is sampled, the weight up-date operation also may occur as often as each new sample arrives, but it takes place between the calculations for the filter output. Thus, a new filter output is first calculated to form the error signal and tht is followed by using that error signal to calculate a new set of increments to add to the weight vector to up-date the weight elements of the filter with the process continually repeating until a point of maximal adaptation has been reached. The updated weight elements $w_{0k+1}$, $w_{1k+1}$, etc., represent the summation of the prior weight values $w_{0k}$, $w_{1k}$ with the product of the current value of the error signal, $E_k$ and the input signal vector samples. The convergence value, $\mu$, is a scaler quantity in the range of from $10^{-4}$ to $10^{-12}$ depending upon the specific application for the adaptive filter. The value of $\mu$ affects the rate at which the system will converge.

Figure 7:
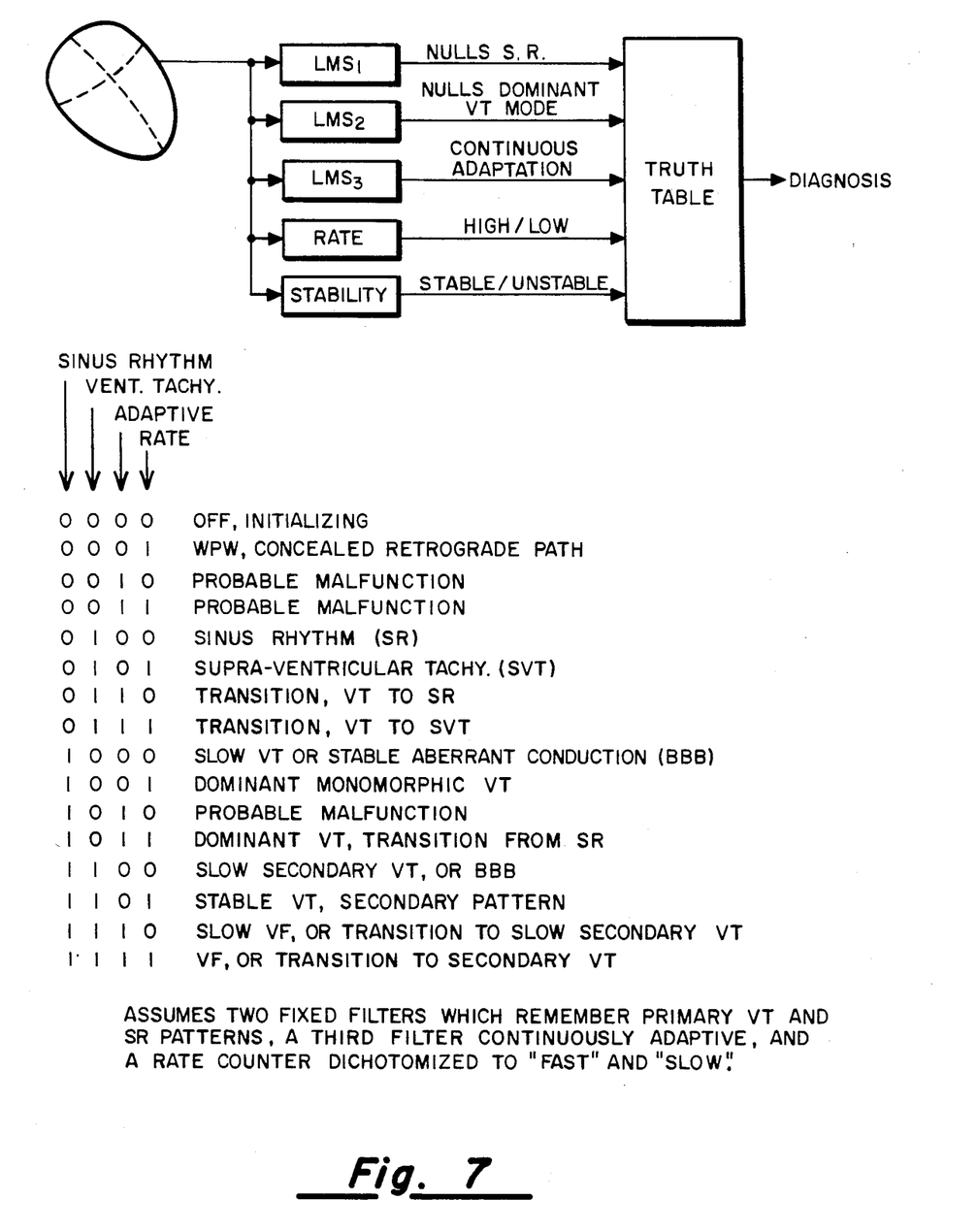
FIG. 7 is a block diagram of a system employing more than one adaptive LMS filter and pulse rate detecting means for identifying/classifying the type of tachyarrhythmia which may be in progress.

Having explained in detail the computational algorithm for implementing the LMS adaptive filter, consideration will next be given to the manner in which the LMS algorithm can be utilized with other conventional techniques in tachyarrhythmia discrimination. In this regard, reference is made to FIG. 7. It shows the outputs of several LMS filters and rate classifiers as inputs to a "truth table" which determines the rhythm. the output of an LMS filter is shown as "0" when the rhythm for which it is tuned is present, or, for continuous adaptation, when the rhythm is sufficiently stable to permit convergence. As an example, a "1001" pattern shows "1" for sinus rhythm filter (rhythm is not SR), a "0" for the primary VT filter (specific to primary VT), a "0" for the adaptive filter (rhythm is stable enough to permit convergence) and a "1", indicating rate is in the tachycardia range. Taken together, these responses indicate primary monomorphic VT. Similarly, if LMS$_1$ produces a null output while LMS$_2$ does not, and the rhythm is stable such that the LMS$_3$ filter converges, and the rate is high, supraventricular tachycardia is indicated. The other truth table entries shown in FIG. 7 define other modalities.

Figure 8A:
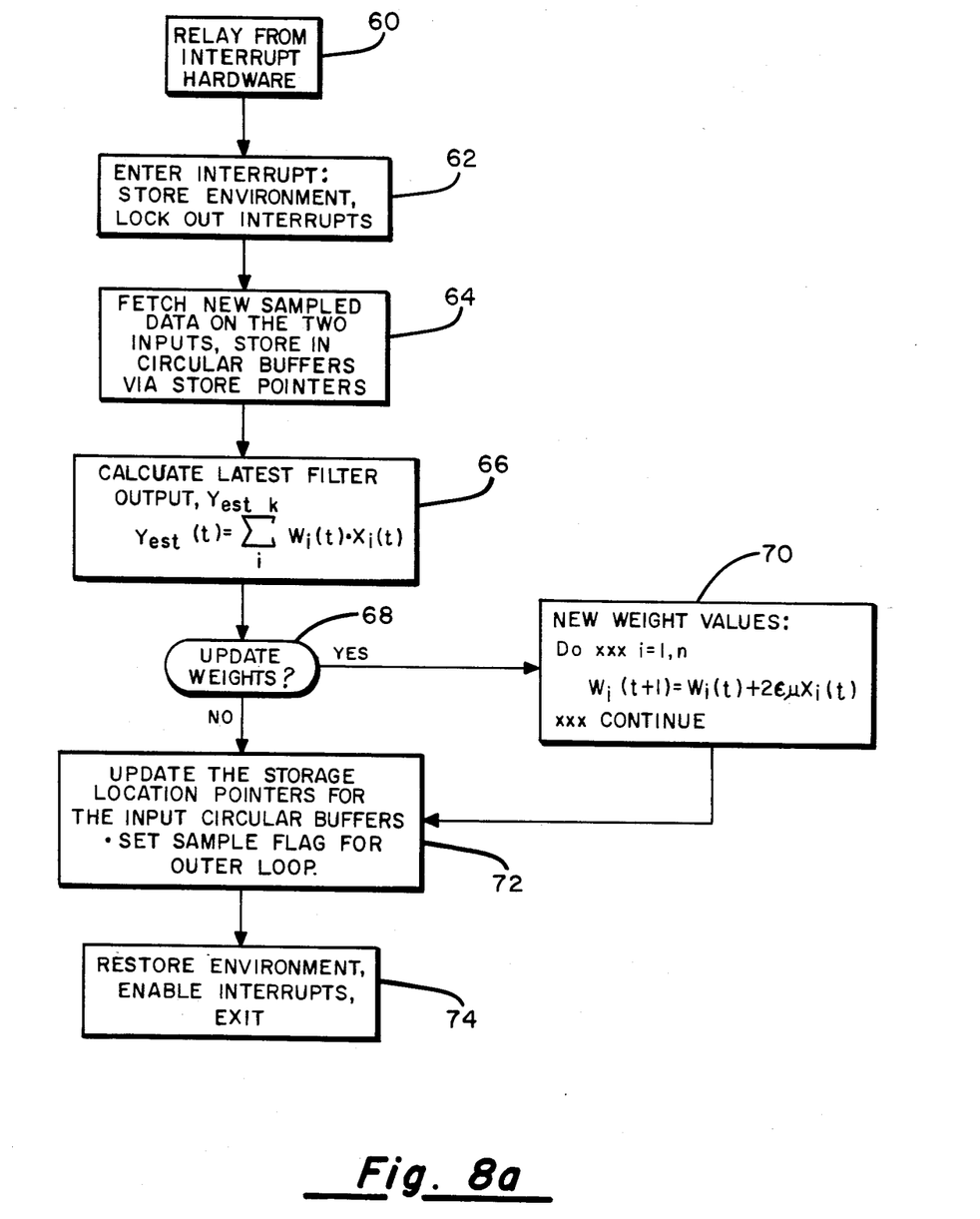
FIGS. 8(a) and 8(b) comprise a flow chart of the software executed by a general purpose digital computer for carrying out the method of the present invention.
Figure 8B:
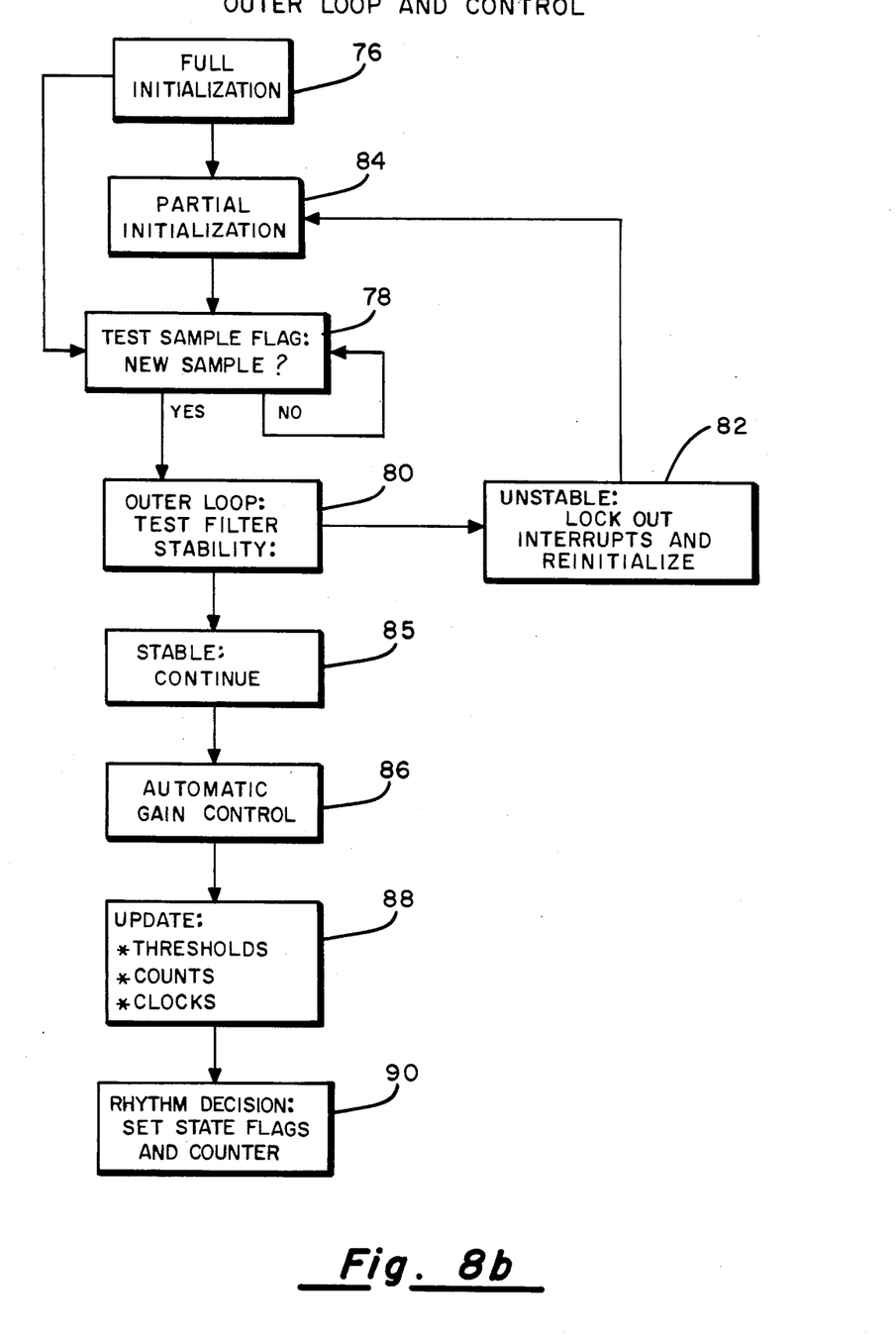

FIGS. 8(a) and 8(b) together comprise a flow chart of the program executable in a general purpose digital computer to implement the adaptive filtering and control whereby fibrillation and tachyarrhythmias discrimination can be achieved. For ease of explanation, the software is partitioned into an inner loop and an outer loop, the inner loop being shown in FIG. 8(a) and the outer loop in FIG. 8(b). The operations performed in the inner loop are initiated by the generation of an interrupt which is occasioned by the outputs from a sample clock or timer in the microprocessor hardware. This sample clock oversees the digitization process by the A-to-D converter, which may typically comprise a sample-and-hold circuit used to periodically capture the magnitude of these analog signals on the endocardial leads positioned within the right ventricle. When the sample-and-hold circuit is triggered to capture a new value, an interrupt is generated to the microprocessor causing the main control program to shift to the inner loop which then executes as an interrupt driven subroutine. Block 60 represents a vectored interrupt stimulated by the sampling clock. In accordance with standard interrupt procedure, as indicated by block 62, when the interrupt is true, the values contained in various registers in the microprocessor are stored so that when the interrupt subroutine is completed, control can return to the point in the program where it left off at the time that the vectored interrupt occurred. For example, the contents of the program counter and other operational registers are stored temporarily. Once this operation has been performed, the operations, identified in block 64 are executed. Specifically, a new sample of the input signal following its conversion from analog-to-digital form is brought into the microprocessor and stored away in a memory so as to become accessible to the arithmetic/logic portion of the microprocessor.

In that in the present application, many samples of input data are simultaneously stored, it has been found convenient to utilize a so-called circular buffer, again, in accord with standard software techniques. It is to be recognized that the buffer needs to hold as many samples of the digitized input data as there are weights on the adaptive filter and these weights must periodically be updated. Using a circular buffer, the address pointer is used to address the part of the circular buffer where the next sample is to be stored or where the next sample is to be fetched for performing an arithmetic operation.

As represented by block 66, the next operation in the inner loop is to calculate the lastest filter output, Y$_{est}$ where Y$_{est}$, at time t, is equal to the summation over the range of i=1 to k of the products of the current weights w$_i$(t) and x$_i$(t), the current data input value. When it is considered that the index, i, can be the address in the circular buffer referred to by the pointer, it can be seen that if the weight values are stored at sequential locations in the buffer, they may be read out in synchrony with the input samples contained in a like buffer similarly addressed but with an address offset and presented to the arithmetic logic unit where the sum of the products operation set out in box 66 of FIG. 8(a) is carried out. The computed result, y$_{est}$(t) is the "estimate" output from the LMS filter 52 (FIG. 4). Following the calculation of the latest filter output as represented by block 66 in the flow diagram, a test is made at 68 to determine whether the weights are to be updated. In performing this decision, a test is made of a flag which is either in a set or a cleared condition depending upon the control exercised by the external program. For example, if the flag always remains set, the weights will be updated each time the filtering operation is executed. If the signals X$_k$ and d$_k$ are sufficiently stable, computation time may be saved by setting the "update weights" flag only periodically, say every tenth sample or, alternatively, it may be set in response to some external condition, such as a rapid transition in heart rate from SR to VT.

Assuming that the flag is set and that the weights are to be updated, the operation, for which the Fortran "Do" statement in box 70 is illustrative, is carried out by the microprocessor. Following that, the storage location pointers for the input circular buffers are updated and the sample flag for the outer loop is set (block 72). Finally, as represented by block 74, the program exits the interrupt routine once the program counter and other registers whose contents had been stored in the operation of the block 62 have been restored their appropriate registers. This completes the inner loop subroutine.

The outer loop depicted in FIG. 8(b) depicts the software operations which are primarily "housekeeping" in nature. At the time that the system of the present invention is put into operation, a step referred to as "full initialization" (block 76) is carried out. It is at this time that certain parameters are initially loaded into memory or holding registers associated with the microprocessor. For example, such things as adaptation time, bandwidth and the number of weights in the filter are established. Following that, once the system is brought into operation, the "sample flag" is evaluated to determine whether a new sample is available from the A-to-D converter. This test is represented in the flow diagram by block 78. It will be recalled that it was during the operations represented by block 72 in the inner loop subroutine of FIG. 8(a) that the "sample flag" for the outer loop was set. If no new test sample is available, the outer loop goes into a wait mode until such time as a new sample is available. At that time, the operation represented by block 80 in FIG. 8(b) is carried out. Specifically, a test is made to determine whether the absolute value of the error plus the absolute value of the estimate is much greater than the absolute value of the desired signals (FIG. 4). If so, it is an indication that the filter is no longer stable indicative of a problem requiring reinitialization. When it has been determined that the system has lost stability, further interrupts to the inner loop are locked out and the system is reinitialized (blocks 82 and 84). In partial initialization, typically the tap-weights for the filter will be reloaded from memory in the pattern indicating convergence to sinus rhythm.

Where it is determined that the filter is stable, the sequence progresses to block 86 which is the operation of "automatic gain control". Since in accordance with the LMS adaptive filter algorithm, the "error" is equal to "desired" minus "estimate", it necessarily follows that the "error" plus the "estimate" is equal to the "desired" signal. Now, by normalizing, i.e., dividing through by the "desired" signal for every sample point, two fractional values are obtained, one for the "error" and one for the "estimate", and their sum is always equal to unity. As previously described, where there is a perfect accommodation to the input signal, substantially all of the energy will be in the "estimated" signal such that when the "estimated" signal is subtracted from the "desired" signal, the "error" signal has essentially zero energy. If then it is later determined that there is substantial energy in the "error" signal relative to the "estimate" signal, one of three situations are indicated. First, the heart may be in a transition between rhythms. Secondly, it may have happened that the filter has diverged and is no longer operating properly. The third and most probable event is that ventricular fibrillation is involved precluding the LMS adaptive filter from accommodating the continuously changing vector characteristic of ventricular fibrillation.

The stabilized outputs (desired, estimate, error) are processed for pulse detection, beat-to-beat interval and variation and interchannel pulse coincidence. During stable rhythms, the "estimate" will coincide with the "desired", and the "error" output will be below some predetermined threshold. During transistions between stable rhythms, the error output will be pulsatile and above that threshold. During unstable rhythms, e.g., VF, the "error" output will be above threshold and there will be asynchrony between the "desired", the "estimate" and the "error" channels. The operation indicated by block 88 indicates the necessity of keeping track of the duration of the period in which the "error" signal approaches or exceeds the threshold and, in this regard, a clock register in the microprocessor is utilized. A counter is also used to keep track of how many pulse may occur during a given length of time. The thresholds, counts and clocks thus need to be periodically updated when it is considered that the system of the present invention is utilized for detecting shifts in rhythms over extended time periods.

Finally, once a determination as to the nature of the rhythm involved has been determined, the microprocessor sets one or more "state" flag (block 90) so that this information becomes available to an external device to be controlled, such as, a defibrillator or a pacemaker.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modification, both as to equipment details and operating procedures, can be accomplished without departing from the scope of the invention itself. In particular, those skilled in the art will realize that the invention can not only be practiced using a programmed digital computer, but also can be implemented using special purpose digital logic devices (hardware).

What is claimed is:

1. Cardiac monitoring apparatus for identifying a variety of cardiac arrhythmias comprising:
   (a) a first pair of electrodes for sensing cardiac electrical activity at a localized site within a cardiac chamber;
   (b) a second pair of electrodes for sensing cardiac electrical activity at a generalized site within said cardiac chamber and producing a reference signal proportional thereto;
   (c) variable transfer function LMS adaptive filler means having an input and an output;
   (d) means for receiving said reference signal and said output from said variable transfer function LMS adaptive filter means for developing an error signal proportional to the difference between said reference signal and said output from said variable transfer function LMS adaptive filter means;
   (e) means coupling said second pair of electrodes to said input to said variable transfer function LMS adaptive filter means; and correlator
   (f) means for comparing the amplitude of the error signal emanating from said variable transfer function LMS adaptive filter means with a predetermined threshold value for discriminating between plural types of tachyarrhythmias and ventricular fibrillation.

2. The cardiac monitoring apparatus as in claim 1 wherein said variable transfer function LMS adaptive filter means comprises:
   (a) input signal delay means for sequentially presenting said sample input to variable gain devices;
   (b) means for summing the outputs from said variable gain devices at predetermined times to form an estimate of a desired signal;
   (c) means for successively algebraically adding said estimated desired signal to said reference input to form said error signal; and means for applying said error signal to said variable gain devices for adjusting the gain values thereof.

3. A method of assessing cardiac tachycardia or comprising:
   (a) first sensing cardiac electrical activity in a first location within the heart;
   (b) second sensing cardiac electrical activity in a second location within the heart;
   (c) continuously applying signals related to said electrical activity from said first and second sensing steps as a desired signal, $d_k$, and as an input signal $X_k$, to an adaptive LMS filter;
   (d) deriving an estimate signal, $Y_k$, from said adaptive LMS filter;
   (e) deriving an error signal, $E_k$, from said desired and estimate signals in accordance with the equation:

$$E_k = d_k - Y_k$$

where k is a time index, $d_k$ is the desired signal at time k and $Y_k$ is the product of a changeable weight vector, $w_k$, and said input signal vector $X_k$, said error signal having a predetermined characteristic upon the occurrence tachycardia or ventricular fibrillation.

4. The method as in claim 3 and further including the step of periodically updating said weight vector, $W_k$, in accordance with the formula:

$$w_{k+1} = W_k + 2\mu E_k X_k$$

where $\mu$ is an adaptation time constant.

* * * * *

UNITED STATES PATENT AND TRADEMARK OFFICE
CERTIFICATE OF CORRECTION

PATENT NO. : 4,799,493

DATED : January 24, 1989

INVENTOR(S) : Robert A. DuFault

It is certified that error appears in the above-identified patent and that said Letters Patent is hereby corrected as shown below:

Column 12, line 3, change "filler" to -- filter --.
Column 12, line 24, change "tachycardia or" to
-- arrhythmias --.

Signed and Sealed this

Twentieth Day of June, 1989

Attest:

DONALD J. QUIGG

Attesting Officer

Commissioner of Patents and Trademarks